United States Patent [19]

Schmid et al.

[11] 4,418,217

[45] Nov. 29, 1983

[54] MIXED FORMALS OF POLYGLYCOL ETHERS

[75] Inventors: Karl Schmid, Mettmann; Margarete Grünert, Kaarst; Jochen Heidrich; Holger Tesmann, both of Dusseldorf, all of Fed. Rep. of Germany

[73] Assignee: Henkel Kommanditgesellschaft auf Aktien, Dusseldorf-Holthausen, Fed. Rep. of Germany

[21] Appl. No.: 257,632

[22] Filed: Apr. 27, 1981

[30] Foreign Application Priority Data

May 12, 1980 [DE] Fed. Rep. of Germany ....... 3018135

[51] Int. Cl.$^3$ ...................... C07C 41/14; C07C 43/11
[52] U.S. Cl. .................................... 568/593; 568/600; 568/601; 568/603; 253/174.21; 253/351
[58] Field of Search ................ 568/593, 601, 603, 600

[56] References Cited

U.S. PATENT DOCUMENTS

| | | | |
|---|---|---|---|
| 2,321,557 | 6/1943 | Sussman | 568/601 |
| 2,397,514 | 4/1946 | Staff | 568/593 |
| 2,796,423 | 6/1957 | Cottle et al. | 568/601 X |
| 2,838,573 | 6/1958 | Matuszak et al. | 568/601 |
| 2,905,718 | 9/1959 | de Benneville et al. | 568/593 X |
| 2,905,719 | 9/1959 | de Benneville et al. | 568/601 X |
| 2,905,720 | 9/1959 | de Benneville et al. | 568/601 X |
| 2,979,533 | 4/1961 | Bruson et al. | 568/601 X |

FOREIGN PATENT DOCUMENTS

| | | | |
|---|---|---|---|
| 283112 | 11/1928 | United Kingdom | 568/594 |
| 1488108 | 10/1977 | United Kingdom | |
| 2017100 | 10/1979 | United Kingdom | 568/601 |

Primary Examiner—Bernard Helfin
Attorney, Agent, or Firm—Hammond & Littell, Weissenberger and Muserlian

[57] ABSTRACT

A process for the production of a mixed formal of polyglycol ethers having formulae selected from the group consisting of $$R^1-CH-O-(A-O)_m-CH_2-(O-B)_q-O-R^4$$
$$R^2-CH-O-(A-O)_n-CH_2-(O-B)_q-O-R^4$$

and $$R^3-O-(A-O)_p-CH_2-(O-B)_q-O-R^4$$

wherein $R^1$ is a straight or branched chain alkyl having from 1 to 18 carbon atoms, and $R^2$ is selected from the group consisting of hydrogen and straight or branched chain alkyl having from 1 to 17 carbon atoms, where the sum of the carbon atoms in $R^1$ plus $R^2$ is from 6 to 18, $R^3$ is a member selected from the group consisting of monoalkylphenyl having from 14 to 26 carbon atoms, dialkylphenyl having from 14 to 26 carbon atoms, trialkylphenyl having from 14 to 26 carbon atoms, a straight or branched chain alkyl having from 8 to 22 carbon atoms, a straight or branched chain alkenyl having from 8 to 22 carbon atoms, and a radical having the formula

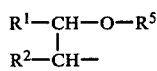

wherein $R^1$ and $R^2$ have the above assigned values, and $R^5$ is selected from the group consisting of a straight or branched chain alkyl having from 1 to 5 carbon atoms, phenyl and alkylphenyl having from 7 to 9 carbon atoms, $R^4$ is a straight or branched chain alkyl having from 1 to 5 carbon atoms, A and B are selected from the group consisting of ethylene and isopropylene, m and n are integers from 0 to 50, p is an integer from 2 to 50, and q is an integer from 0 to 3, where the sum of m plus n is from 2 to 50, consisting essentially of the steps of (1) reacting a polyglycol ether having the formulae selected from the group consisting of

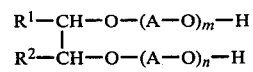

and

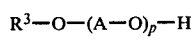

wherein $R^1$, $R^2$, $R^3$, A, m, n and p have the above-assigned meanings, with a diformal having the formula

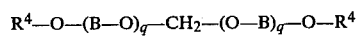

wherein $R^4$, B and q have the above-assigned meanings, at a temperature of from 60° to 150° C. in the presence of a strong acid, while employing from 2 to 10 mols of said diformal per mol of hydroxyl groups in said polyglycol ether.

(2) distilling off the alcohol formed having the formula

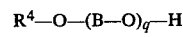

(3) neutralizing, (4) distilling of unreacted diformal, and (5) recovering said mixed formal of polyglycol ethers; as well as novel mixed formals of polyglycol ethers produced by the process.

7 Claims, No Drawings

MIXED FORMALS OF POLYGLYCOL ETHERS

The subject matter of the invention is an improved process for the preparation of a mixed formal of polyglycolethers by reacting polyglycolethers with symmetrical acetals (formals) formed of formaldehyde and alcohols, alkylglycolethers and alkylpolyglycolethers.

British Pat. No. 1,488,108 describes a process for the preparation of polyglycolether mixed formals where addition products of alkylene oxides onto long chain aliphatic alcohols or monoalkylphenols, dialkylphenols and trialkylphenols are reacted with a short-chain alcohol and formaldehyde. The products obtained have surface-active properties and are suitable as tensides for wetting, washing and cleansing agents. These end group blocked polyglycolether derivatives offer considerable advantages, like low-sudsing and high alkali stability with biodegradability, as compared to polyglycolethers having free terminal hydroxyl groups.

In the preparation of the polyglycolethers according to British Pat. No. 1,488,108, 1 mol of an alkylpolyglycolether or alkenylpolyglycolether or phenylpolyglycolether is reacted with heating with 3 to 5 mols of an alcohol and 0.5 to 1 mol of formaldehyde in the presence of a strong acid, with the elimination of the dialkyl formal and the water of reaction formed.

It has been found that the polyglycolether mixed formals obtained this way are contaminated with considerable amounts of polyglycolether. For this reason the products obtained this way have only a low alkali-stability and turn brown to black within 24 hours when stored over powdered caustic soda at 90° C. Another drawback of these products is their formaldehyde odor.

OBJECTS OF THE INVENTION

An object of the present invention is to find an improved process for the preparation of mixed formals of polyglycolethers, which gives high purity, alkali-stable and odorless products of high color quality. This object is solved with the process described below.

Another object of the present invention is the development of a process for the production of a mixed formal of polyglycol ethers having formulae selected from the group consisting of $$R^1-CH-O-(A-O)_m-CH_2-(O-B)_q-O-R^4$$
$$R^2-CH-O-(A-O)_n-CH_2-(O-B)_q-O-R^4$$

and $$R^3-O-(A-O)_p-CH_2-(O-B)_q-O-R^4$$

wherein $R^1$ is a straight or branched chain alkyl having from 1 to 18 carbon atoms, and $R^2$ is selected from the group consisting of hydrogen and straight or branched chain alkyl having from 1 to 17 carbon atoms, where the sum of the carbon atoms in $R^1$ plus $R^2$ is from 6 to 18, $R^3$ is a member selected from the group consisting of monoalkylphenyl having from 14 to 26 carbon atoms, dialkylphenyl having from 14 to 26 carbon atoms, trialkylphenyl having from 14 to 26 carbon atoms, a straight or branched chain alkyl having from 8 to 22 carbon atoms, a straight or branched chain alkenyl having from 8 to 22 carbon atoms, and a radical having the formula

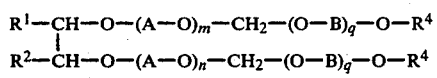

wherein $R^1$ and $R^2$ have the above assigned values, and $R^5$ is selected from the group consisting of a straight or branched chain alkyl having from 1 to 5 carbon atoms, phenyl and alkylphenyl having from 7 to 9 carbon atoms, $R^4$ is a straight or branched chain alkyl having from 1 to 5 carbon atoms, A and B are selected from the group consisting of ethylene and isopropylene, m and n are integers from 0 to 50, p is an integer from 2 to 50, and q is an integer from 0 to 3, where the sum of m plus n is from 2 to 50, consisting essentially of the steps of (1) resisting a polyglycol ether having the formulae selected from the group consisting of $$R^1-CH-O-(A-O)_m-H$$
$$R^2-CH-O-(A-O)_n-H$$

and $$R^3-O-(A-O)_p-H$$

wherein $R^1$, $R^2$, $R^3$, A, m, n and p have the above-assigned meanings, with a diformal having the formula $$R^4-O-(B-O)_q-CH_2-(O-B)_q-O-R^4$$

wherein $R^4$, B and q have the above-assigned meanings, at a temperature of from 60° to 150° C. in the presence of a strong acid, while employing from 2 to 10 mols of said diformal per mol of hydroxyl groups in said polyglycol ether.

(2) distilling off the alcohol formed having the formula $$R^4-O-(B-O)_q-H$$

(3) neutralizing,
(4) distilling of unreacted diformal, and
(5) recovering said mixed formal of polyglycol ethers.

A yet further object of the invention is the development of a mixed formal of polyglycol ethers having formulae selected from the group consisting of $$R^1-CH-O-(A-O)_m-CH_2-(O-B)_q-O-R^4$$
$$R^2-CH-O-(A-O)_n-CH_2-(O-B)_q-O-R^4$$

and $$R^6-O-(A-O)_p-CH_2-(O-B)_q-O-R^4$$

wherein $R^1$ is a straght or branched chain alkyl having from 1 to 18 carbon atoms, and $R^2$ is selected from the group consisting of hydrogen and straight or branched chain alkyl having from 1 to 17 carbon atoms, where the sum of the carbon atoms in $R^1$ plus $R^2$ is from 6 to 18, $R^6$ is a radical having the formula

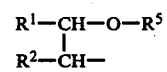

wherein $R^1$ and $R^2$ have the above assigned values, and $R^5$ is selected from the group consisting of a straight or branched chain alkyl having from 1 to 5 carbon atoms, phenyl and alkylphenyl having from 7 to 9 carbon atoms, $R^4$ is a straight or branched chain alkyl having from 1 to 5 carbon atoms, A and B are selected from the group consisting of ethylene and isopropylene, m and n are integers from 0 to 50, p is an integer from 2 to 50, and q is an integer from 0 to 3, where the sum of m plus n is from 2 to 50.

These and other objects of the invention will become more apparent as the description thereof proceeds.

DESCRIPTION OF THE INVENTION

The subject matter of the invention is a process for the preparation of a mixed formal of polyglycolethers of Formula I or II $$R^1-CH-O-(A-O)_m-CH_2-(O-B)_q-O-R^4 \quad \text{I}$$
$$R^2-CH-O-(A-O)_n-CH_2-(O-B)_q-O-R^4$$

$$R^3-O-(A-O)_p-CH_2-(O-B)_q-O-R^4 \quad \text{II}$$

where $R^1$ stands for a linear or branched alkyl with 1 to 18 carbon atoms and $R^2$ stands for hydrogen or a linear or branched alkyl with 1 to 17 carbon atoms, where the sum of the carbon atoms in $R^1$ and $R^2$ is 6 to 18; $R^3$ denotes a monoalkylphenyl, dialkylphenyl, or trialkylphenyl having from 14 to 26 carbon atoms, a linear or branched alkyl with 8 to 22 carbon atoms, or a radical of Formula III $$R^1-CH-O-R^5 \quad \text{III}$$
$$R^2-CH-$$

wherein $R^1$ and $R^2$ have the above-indicated meanings and $R^5$ denotes a linear or branched alkyl with 1 to 5 carbon atoms, phenyl or alkylphenyl with 6 to 9 carbon atoms; while $R^4$ denotes a linear or branched alkyl with 1 to 5 carbon atoms; A and B denote ethylene or isopropylene; m and n are numbers from 0 to 50; p is a number from 2 to 50; and q is a number from 0 to 3, where the sum of $m+n=2$ to 50, characterized in that polyglycolethers of Formula IV or V $$R^1-CH-O-(A-O)_m-H \quad \text{IV}$$
$$R^2-CH-O-(A-O)_n-H$$

$$R^3-O-(A-O)_p-H \quad \text{V}$$

where $R^1$, $R^2$, $R^3$, A, m, n and p have the above-indicated meanings, are reacted with a diformal of Formula VI $$R^4-O-(B-O)_q-CH_2-(O-B)_q-O-R^4 \quad \text{VI}$$

where $R^4$, B and q have the above-indicated meaning, at temperatures of from 60° to 150° C. in the presence of a strong acid, using 2 to 10 mols of said diformal per mol of hydroxyl groups contained in Formula IV or V; the alcohol $R^4O-(B-O)_qH$, formed in the reaction is distilled off together, if necessary with diformal from the reaction mixture, the acid remaining in the residue being neutralized or removed, if necessary, by filtration while the remaining diformal is distilled off and any salts that are present are removed by filtration.

More particularly, the present invention relates to a process for the production of a mixed formal of polyglycol ethers having formulae selected from the group consisting of $$R^1-CH-O-(A-O)_m-CH_2-(O-B)_q-O-R^4$$
$$R^2-CH-O-(A-O)_n-CH_2-(O-B)_q-O-R^4$$

and $$R^3-O-(A-O)_p-CH_2-(O-B)_q-O-R^4$$

wherein $R^1$ is a straight or branched chain alkyl having from 1 to 18 carbon atoms, and $R^2$ is selected from the group consisting of hydrogen and straight or branched chain alkyl having from 1 to 17 carbon atoms, where the sum of the carbon atoms in $R^1$ plus $R^2$ is from 6 to 18, $R^3$ is a member selected from the group consisting of monoalkylphenyl having from 14 to 26 carbon atoms, dialkylphenyl having from 14 to 26 carbon atoms, trialkylphenyl having from 14 to 26 carbon atoms, a straight or branched chain alkyl having from 8 to 22 carbon atoms, a straight or branched chain alkenyl having from 8 to 22 carbon atoms, and a radical having the formula $$R^1-CH-O-R^5$$
$$R^2-CH-$$

wherein $R^1$ and $R^2$ have the above assigned values, and $R^5$ is selected from the group consisting of a straight or branched chain alkyl having from 1 to 5 carbon atoms, phenyl and alkylphenyl having from 7 to 9 carbon atoms, $R^4$ is a straight or branched chain alkyl having from 1 to 5 carbon atoms, A and B are selected from the group consisting of ethylene and isopropylene, m and n are integers from 0 to 50, p is an integer from 2 to 50, and q is an integer from 0 to 3, where the sum of m plus n is from 2 to 50, consisting essentially of the steps of (1) reacting a polyglycol ether having the formulae selected from the group consisting of $$R^1-CH-O-(A-O)_m-H$$
$$R^2-CH-O-(A-O)_n-H$$

and $$R^3-O-(A-O)_p-H$$

wherein $R^1$, $R^2$, $R^3$, A, m, n and p have the above-assigned meanings, with a diformal having the formula $$R^4-O-(B-O)_q-CH_2-(O-B)_q-O-R^4$$

wherein $R^4$, B and q have the above-assigned meanings, at a temperature of from 60° to 150° C. in the presence of a strong acid, while employing from 2 to 10 mols of said diformal per mol of hydroxyl groups in said polyglycol ether.

(2) distilling off the alcohol formed having the formula $$R^4-O-(B-O)_q-H$$

(3) neutralizing,
(4) distilling of unreacted diformal, and
(5) recovering said mixed formal of polyglycol ethers.

The polyglycolethers of Formula IV and V used as starting material are known substances which can be obtained according to known methods by adducting ethylene oxide and propylene oxide onto vicinal alkanediols, monoalkylethers, or monoarylethers of vicinal alkanediols, monoalkylphenols, dialkylphenols or trialkylphenols and long-chain aliphatic alcohols.

Vicinal alkanediols can be obtained, for example, by epoxidation of corresponding olefins and subsequent hydrolysis of the resulting epoxyalkanes. Suitable vicinal alkanediols for the preparation of the above-mentioned polyglycolethers are, for example, octanediol-1,2, nonanediol-1,2, decanediol-1,2, dodecanediol-1,2, hexadecanediol-1,2, octadecanediol-1,2, eicosanediol-1,2, mixtures of alkanediols-1,2 with a chain length of $C_{12}$–$C_{14}$, mixtures of alkanediols-1,2 with a chain length of $C_{16}$–$C_{18}$, mixtures of isomeric vicinal alkanediols of the chain length $C_{10}$ with non-terminal hydroxyl groups, mixtures of isomeric vicinal alkanediols of the chain length $C_{18}$ with non-terminal hydroxyl groups, mixtures of isomeric vicinal alkanediols of the chain length $C_{11}$–$C_{15}$ with non-terminal hydroxyl groups, mixtures of isomeric vicinal alkanediols of the chain length $C_{14}$–$C_{16}$ with non-terminal hydroxyl groups, and mixtures of isomeric vicinal alkanediols of the chain length $C_{15}$–$C_{18}$ with non-terminal hydroxyl groups.

Monoalkyl, monoaryl, and monoalkylaryl ethers of the above-mentioned alkanediols can be obtained, for example, from corresponding epoxyalkanes by reacting with the corresponding aliphatic alcohols, phenol and alkylphenols. Epoxy alkanes which can be used are, for example, 1,2-epoxyoctane, 1,2-epoxydodecane, 1,2-epoxytetradecane, 1,2-epoxyhexadecane, 1,2-epoxyoctadecane, 1,2-epoxyeicosane, mixtures of 1,2-epoxyalkanes of the chain length $C_{12}$–$C_{14}$, mixtures of 1,2-epoxyalkanes of the chain-length $C_{16}$–$C_{18}$, mixtures of isomeric epoxyalkanes of the chain length $C_{10}$ with a non-terminal epoxy group, mixtures of isomeric epoxyalkanes of the chain length $C_{18}$ with a non-terminal epoxy group, mixtures of isomeric epoxyalkanes of the chain length $C_{11}$–$C_{15}$ with a non-terminal epoxy group, mixtures of isomeric epoxyalkanes of the chain length $C_{14}$–$C_{16}$ with a non-terminal epoxy group, and mixtures of isomeric epoxyalkanes of the chain length $C_{15}$–$C_{18}$ with a non-terminal epoxy group. Suitable alcohols for the reaction of these epoxyalkanes to the corresponding beta-hydroxy-ethers are, for example, methanol, ethanol, propanol, butanol, phenol, o-cresol, p-cresol, ethyleneglycol and isopropyleneglycol.

The phenols which are suitable for the preparation of the above-mentioned polyglycolethers are, for example, octylphenol, octylcresol, nonylphenol, dodecylphenol, tributylphenol and dinonylphenol.

Examples of suitable fatty alcohols are n-octanol, n-decanol, n-dodecanol, n-tetradecanol, n-hexadecanol and n-octadecanol. As a rule, however, the synthesis of the polyglycolethers used as starting material is effected with fatty alcohol mixtures, as they are obtained in the sodium reduction or the catalytic hydrogenation of fatty acid mixtures obtained from native fats, oils, and waxes, such as the technical coconut fatty alcohols, palm kernel fatty alcohols, tallow fatty alcohols, soybean oil fatty alcohols, and linseed oil fatty alcohols. These alcohols are mixtures of higher alkanols, alkenols and alkadienols. Furthermore, mixtures of synthetic alkanols which are obtained from petroleum products according to the Ziegler- or the oxo-process can also be used, also mixtures primarily of secondary alkanols, which are obtained by atmospheric oxidation of linear paraffins in the presence of boric acid or boric acid anhydride.

In the preparation of the polyglycolethers used as starting material, the compound containing the hydroxyl groups are reacted in known manner at elevated temperature and elevated pressure in the presence of suitable alkoxylation catalysts with corresponding amounts of an alkylene oxide, such as ethylene oxide or propylene oxide. The epoxides can be utilized either individually or in admixtures. They can also be added successively in any desired order. Among the mixed ethylene oxide/propylene oxide addition products, those are preferred, because of their favorable application properties, where the alkoxy units consist of ethoxy units with up to 20 mol % of isopropoxy units.

The diformals of Formula VI used as starting material in the process according to the invention represent, likewise, a known category of substances. They are preferably prepared by acetalation of formaldehyde with alcohols or alkylalkyleneglycolethers at elevated temperature and in the presence of a strong acid. Alcohols which can be used are primarily methanol, ethanol, n-propanol and particularly butanol. Examples of suitable alkylalkyleneglycolethers are the addition products of 1 to 3 mol of ethylene oxide or propylene oxide onto the above-mentioned alcohols.

In carrying out the process according to the invention, the reaction partners react with each other in the presence of a strong acid. Here, phosphoric acid, p-toluene-sulfonic acid, acid organic ion-exchangers, and acid zeolites, and preferably sulfuric acid are used with advantage. It was found advisable to use the strong acid in an amount of 0.05 to 0.5% by weight, based on the polyglycolether to be reacted.

The process according to the invention is carried out in reaction vessels which permit distillation of the free alcohol formed and of the excess diformal, preferably under reduced pressure. For batches on a technical scale, it is of advantage to stir the reaction mixture during heating. The reaction is generally carried out at temperatures of 60° to 150° C., preferably to 70° to 100° C.

An essential feature of the process according to the invention is that the alcohol formed in the reaction between the polyglycolether and the symmetrical diformal is removed from the reaction mixture prior to neutralization or filtration of the acid catalyst. This can be done by heating the reaction mixture until the reaction between the polyglycolether and the symmetrical diformal is completed, then distilling off the alcohol formed. When using simple distillation apparatus, a part of the diformal excess distills over with the free alcohol. A clear separation of the alcohols formed can be obtained by means of a correspondingly dimensioned distillation column. Particularly favorable in this respect is the process according to the invention if symmetrical diformals of Formula VI are used, in which q has the value 1 to 3. The alcohols $R^4$—O—(B—O)$_q$—H formed in this case can be withdrawn from the reaction mixture without diformal distilling over.

After the free alcohol has been removed, the acid contained in the reaction mixture is neutralized by the addition of a basic substance, such as sodium hydroxide or potassium hydroxide, potassium carbonate, or preferably sodium methylate in methanol solution. Subsequently, the diformal not used up during the reaction is distilled off, preferably under reduced pressure.

The mixed formals remaining as residue can be used directly in those cases where the existing neutral salts do not interfere. If separation of the salts is indicated, this can be effected by simple filtration, if necessary, by using a filtration aid.

The mixed formals of polyalkyleneglycolethers of Formula I, as well as the compounds of Formula II, where $R^3$ has the meaning indicated in Formula III, are new substances. The novel compounds are a mixed formal of polyglycol ethers having formulae selected from the group consisting of

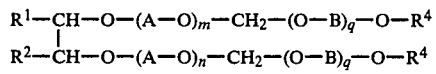

and

wherein $R^1$ is a straight or branched chain alkyl having from 1 to 18 carbon atoms, and $R^2$ is selected from the group consisting of hydrogen and straight or branched chain alkyl having from 1 to 17 carbon atoms, where the sum of the carbon atoms in $R^1$ plus $R^2$ is from 6 to 18, $R^6$ is a radical having the formula

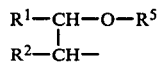

wherein $R^1$ and $R^2$ have the above assigned values, and $R^5$ is selected from the group consisting of a straight or branched chain alkyl having from 1 to 5 carbon atoms, phenyl and alkylphenyl having from 7 to 9 carbon atoms, $R^4$ is a straight or branched chain alkyl having from 1 to 5 carbon atoms, A and B are selected from the group consisting of ethylene and isopropylene, m and n are integers from 0 to 50, p is an integer from 2 to 50, and q is an integer from 0 to 3, where the sum of m plus n is from 2 to 50.

The mixed formals of polyalkyleneglycolethers obtained according to the process of the invention are odorless and are obtained with OH-numbers ranging from 0 to 6. In contrast to mixed formals obtained according to a conventional process, they are extremely stable in the presence of strong alkalies, such as alkali metal hydroxides, alkali metal silicates and alkali metal phosphates. Thus samples of the mixed formals prepared according to the invention can be stored for 3 days at 90° C. over caustic soda without decomposition or discoloration.

The mixed formals of Formula I and II are surface-active substances with excellent cleaning power and an extremely low tendency to foaming. Beyond that, they are biodegradable. Due to this property, they are particularly suitable for the production of rinses and industrial cleansers. Furthermore, the mixed formals obtained according to the invention are suitable for use in liquid or solid detergents and cleansers. They can be used either alone or in combination with other known non-ionic, cationic, anionic or zwitterionic surface-active substances, builders, and other additives or assistants in detergent and cleanser formulas.

The content of compounds of Formula I and II in the detergent and cleanser formulas can vary within wide limits. Depending on their use and on the conditions under which the detergents and cleansers are used, their content of mixed formals can vary between 1% and 30% by weight, preferably between 2% and 10% by weight.

The following examples will illustrate the subject of the invention without limiting it, however, to these examples.

EXAMPLE 1

86.2 kg (1162.7 mols) of butanol, 19.6 kg (654.0 mols) of paraformaldehyde and 54.5 ml of conc. sulfuric acid were heated to about 100° C. in an agitator vessel equipped with agitator, inside thermometer and reflux condenser. The heating was continued for a period until 10.46 kg of water were separated by azeotropic distillation. After cooling, the remaining acid was neutralized by the addition of 180 gm of a 30% by weight sodium methylate solution. After the addition of 100 gm of solid potassium carbonate, the reaction product was subjected to fractional distillation. 71 kg of dibutyl formal distilled over at 87° C./15 mbar (76% of the theory).

55.8 kg (348.8 mols) of the dibutyl formal obtained, 36.2 kg (58.1 mols) of an adduct of 9 mols of ethylene oxide onto 1 mol of coconut fatty alcohol (mixture of fatty alcohols of the chain length $C_{12}$-$C_{18}$) and 73 gm of conc. sulfuric acid were heated in a distillation apparatus for 2 hours to 80° C. Then the pressure was reduced in the distillation apparatus so far that butanol began to distill off in mixture with dibutyl formal. After 2 hours, 27.9 kg of the butanol-dibutyl formal mixture had distilled over. The remaining mixture was neutralized with sodium methylate. Subsequently the excess dibutyl formal was distilled off, and the sump temperature was increased to 150° C. By filtering off the distillation residue, finally 40 kg of a mixed formal of polyglycolether with an OH-number of 1.1 and a turbidity point of 24° C. were obtained.

EXAMPLES 2-12

The reactions were carried out in analogy to Example 1. In addition to n-dodecanol polyethyleneglycolethers, ethylene oxide adducts and ethylene oxide/propylene oxide adducts of fatty alcohol mixtures were used as a starting material. These polyalkyleneglycolethers are characterized in the following Table I by the fatty alcohol component and the number of added alkylene oxide units (EO-ethylene oxide; PO-propylene oxide). The order of the addition in the ethylene oxide/propylene oxide adducts can be seen from the indication: +8 EO+1 PO. This means that 8 mols of ethylene oxide were added first and then 1 mol of propylene oxide. In the second last and last column of Table I are entered the OH numbers and the turbidity points of the mixed formals obtained.

TABLE I

| Example | Polyglycolether | Dialkylformal | OH-No. | Turbidity point °C. |
|---|---|---|---|---|
| 1 | $C_{12-18}$ Coconut Fatty Alcohol + 9EO | $(C_4H_9O)_2CH_2$ | 1.1 | 24 |
| 2 | Dodecanol + 5 EO | $(C_4H_9O)_2CH_2$ | 0.6 | <0 |
| 3 | Dodecanol + 6 EO | $(C_4H_9O)_2CH_2$ | 1.8 | <0 |
| 4 | Dodecanol + 10 EO | $(C_4H_9O)_2 CH_2$ | 2.0 | 20 |
| 5 | $C_{12-16}$—Fatty alcohol + 9 EO | $(C_4H_9O)_2CH_2$ | 0.3 | 19 |

TABLE I-continued

| Example | Polyglycolether | Dialkylformal | OH-No. | Turbidity point °C. |
|---|---|---|---|---|
| 6 | $C_{12-18}$—Fatty alcohol + 7 EO | $(C_4H_9O)_2CH_2$ | 1.3 | 12 |
| 7 | $C_{12-18}$—Fatty alcohol + 11 EO | $(C_4H_9O)_2CH_2$ | <1 | 26 |
| 8 | $C_{12-18}$—Fatty alcohol + 8 EO + 1 PO | $(C_4H_9O)_2CH_2$ | 1.6 | 17 |
| 9 | $C_{12-18}$—Fatty alcohol + 1 PO + 8 EO | $(C_4H_9O)_2CH_2$ | <1 | <0 |
| 10 | $C_{16-18}$—Fatty alcohol + 20 EO | $(C_4H_9O)_2CH_2$ | 1.1 | 50 |
| 11 | $C_{16-18}$—Fatty alcohol + 30 EO | $(C_4H_9O)_2CH_2$ | <1 | 62 |
| 12 | $C_{12-18}$—Fatty alcohol + 9 EO | $(C_3H_7O)_2CH_2$ | 1.2 | 40 |

EXAMPLE 13

The starting material was a polyalkyleneglycolether mixture obtained by reacting ethyleneglycol with a 1,2-epoxyalkane mixture of the chain length $C_{12}$–$C_{18}$, the addition of 1 mol of propylene oxide and subsequent addition of 19 mols of ethylene oxide. This polyalkyleneglycolether mixture was reacted with dibutylformal as described in Example 1. A mixed formal was obtained with an OH-number of 1.4.

EXAMPLE 14

4248 gm (36 mols) of butoxyethanol (butylglycol), 600 gm (10 mols) of paraformaldehyde and 9.2 gm of conc. sulfuric acid in 500 ml toluene were heated to 110° C. in a three-necked flask equipped with agitator, inside thermometer, and reflux condenser with a water separator, until 324 ml of water had separated by azeotropic distillation. After cooling, the reaction mixture was neutralized at pH 7 to 8 by the addition of sodium methylate solution. During the subsequent distillation, a mixture of toluene and butylglycol distilled over under a water jet vacuum. In the main distillate, 3400 gm of dibutylglycolformal (78% of the theory) were obtained with a boiling point of 95° C./0.1 mbar.

2232 gm (8.9 mols) of the dibutylglycolformal obtained, 827 gm (1.5 mols) of an adduct of 7 mols of ethylene oxide onto one mol of an oxoalcohol mixture of the chain length $C_{14}$–$C_{15}$ and 1.7 gm of conc. sulfuric acid were heated in a distillation flask under a pressure of 0.1 mbar to 80° C. until 332 gm of butylglycol and dibutylglycolformal had distilled over. The remaining mixture was neutralized with sodium methylate. Subsequently 1687 gm of dibutylglycolformal were distilled off under an oil pump vacuum, while the sump temperature was increased to 200° C. The residue was filtered. 1037 gm of a mixed formal of polyglycolether with an OH-number of 2.0 and a turbidity point of 16° C. were obtained.

EXAMPLES 15-23

The reactions were carried out in analogy to Example 14. The polyalkyleneglycolether starting materials were ethylene oxide and ethylene oxide/propylene oxide adducts of fatty alcohol mixtures of the chain length $C_{12}$–$C_{18}$ (coconut fatty alcohol cut) and of the chain length $C_{14}$–$C_{20}$ (tallow fatty alcohol), decanol and nonylphenol. These polyalkyleneglycolethers are characterized in Table II by the alcohol or phenol components and the number of added alkylene oxide units. The order of the addition in the ethylene oxide/propylene oxide adducts is indicated as follows: +8 EO+1 PO. This means that ethylene oxide was added first and then propylene oxide.

TABLE II

| Example | Polyglycolether | Diformal | OH No. | Turbidity point °C. |
|---|---|---|---|---|
| 14 | $C_{14-15}$—Oxo alcohol + 7 EO | $(C_4H_9OC_2H_4O)_2CH_2$ | 2.0 | 16 |
| 15 | $C_{12-18}$—Fatty alcohol + 2 EO | $(C_2H_5OC_2H_4O)_2CH_2$ | 0 | <0 |
| 16 | $C_{12-18}$13 Fatty alcohol + 5 EO | $(C_2H_5OC_2H_4O)_2CH_2$ | 5.3 | 36-40 |
| 17 | $C_{12-18}$—Fatty alcohol + 7 EO | $(C_2H_5OC_2H_4O)_2CH_2$ | 2.5 | 42 |
| 18 | $C_{12-18}$—Fatty alcohol + 7 EO | $(C_4H_9OC_2H_4O)_2CH_2$ | 0.8 | 17 |
| 19 | $C_{12-18}$—Fatty alcohol + 9 EO | $(C_4H_9OC_2H_4O)_2CH_2$ | 1.6 | 29 |
| 20 | $C_{14-20}$—Fatty alcohol + 14 EO | $(C_4H_9OC_2H_4O)_2CH_2$ | 1.4 | 38 |
| 21 | Nonylphenol + 9.5 EO | $(C_4H_9OC_2H_4O)_2CH_2$ | 1.0 | 7.5 |
| 22 | $C_{12-18}$—Fatty alcohol + 8 EO + 1 PO | $(CH_3OCH_2CH(CH_3)O)_2CH_2$ | 1.9 | 37 |
| 23 | Decanol + 3 EO | $(CH_3O(C_2H_4O)_2)_2CH_2$ | 1.0 | 35 |

EXAMPLE 24

The polyalkyleneglycolether mixture described in Example 13 was reacted with dibutylglycolformal in analogy to Example 14. We obtained a mixed formal with an OH-number of 3.7.

EXAMPLE 25

The polyalkyleneglycolether mixed formals designated with A1 to A4 in Table III prepared according to the process of the invention were used to test their resistance to alkali. As reference substances were used the products B1 to B4, which had been obtained from the same polyglycolether according to the process described in British Pat. No. 1,488,108 by reaction with formaldehyde and the corresponding alcohol.

The substances A1 to A4 and B1 to B4 were stored for 3 days at 90° C. over caustic soda. The color of the samples observed thereafter is indicated in the last column of Table III.

TABLE III

| No. | | OH-No. | Turbidity point °C. | Color of Product |
|---|---|---|---|---|
| A1 | $C_{12}H_{25}(EO)_{10}OCH_2OC_4H_9$ | 2 | 20 | water-clear |
| B1 | $C_{12}H_{25}(EO)_{10}OCH_2OC_4H_9$ | 19 | 31 | deep brown |
| A2 | $C_{12}H_{25}(EO)_{15}OCH_2OC_4H_9$ | 0 | 37 | water-clear |
| B2 | $C_{12}H_{25}(EO)_{15}OCH_2OC_4H_9$ | 17 | 50 | deep brown |

TABLE III-continued

| No. | | OH-No. | Turbidity point °C. | Color of Product |
|---|---|---|---|---|
| A3 | $C_{12-18}H_{25-37}(EO)_9OCH_2OC_4H_9$ | 0 | 24 | water-clear |
| B3 | $C_{12-18}H_{25-37}(EO)_9OCH_2OC_4H_9$ | 16 | 33 | deep brown |
| A4 | $C_{12}H_{25}(EO)_{10}OCH_2OC_2H_4OC_4H_9$ | 1 | 24 | water-clear |
| B4 | $C_{12}H_{25}(EO)_{10}OCH_2OC_2H_4OC_4H_9$ | 26 | 33 | deep brown |

It is pointed out that the above-mentioned British Pat. No. 1,488,108 only discloses mixed formals of the formula $$R^3-O-(A-O)_p-CH_2-(O-B)_q-O-R^4$$

where $R^3$ is linear or branched alkyl or alkenyl or mono-, di- or trialkylphenyl and q is 0. Comparison product B4, where q is 1, is not contemplated by the patentees. Products where q is 1 to 3 in Formula II are not disclosed by the patentees.

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. The mixed formal of polyglycol ethers produced by the process consisting essentially of the steps of:

(1) reacting a polyglycol ether having the formulae selected from the group consisting of $$R^1-CH-O-(A-O)_m-H$$
$$R^2-CH-O-(A-O)_n-H$$

and $$R^3-O-(A-O)_p-H$$

wherein $R^1$ is a straight or branched chain alkyl having from 1 to 18 carbon atoms, and $R^2$ is selected from the group consisting of hydrogen and straight or branched chain alkyl having from 1 to 17 carbon atoms, where the sum of the carbon atoms in $R^1$ plus $R^2$ is from 6 to 18, $R^3$ is a member selected from the group consisting of monoalkylphenyl having from 14 to 26 carbon atoms, dialkylphenyl having from 14 to 26 carbon atoms, trialkylphenyl having from 14 to 26 carbon atoms, a straight or branched chain alkyl having from 8 to 22 carbon atoms, a straight or branched chain alkenyl having from 8 to 22 carbon atoms, and a radical having the formula $$R^1-CH-O-R^5$$
$$R^2-CH-$$

wherein $R^1$ and $R^2$ have the above assigned values, and $R^5$ is selected from the group consisting of a straight or branched chain alkyl having from 1 to 5 carbon atoms, phenyl and alkylphenyl having from 7 to 9 carbon atoms, A is selected from the group consisting of ethylene and isopropylene, m and n are integers from 0 to 50, and p is an integer from 2 to 50, where the sum of m plus n, is from 2 to 50. with a diformal having the formula $$R^4-O-(B-O)_q-CH_2-(O-B)_q-O-R^4$$

wherein $R^4$ is a straight or branched chain alkyl having from 1 to 5 carbon atoms, B is selected from the group consisting of ethylene and propylene, and q is an integer from 0 to 3, at a temperature of from 60° to 150° C. in the presence of a strong acid, while employing from 2 to 10 mols of said diformal per mol of hydroxyl groups in said polyglycol ether, (2) distilling off the alcohol formed having the formula $$R^4-O-(B-O)_q-H$$

wherein $R^4$, B and q have the above-assigned values, (3) neutralizing,
(4) distilling of unreacted diformal, and
(5) recovering said mixed formal of polyglycol ethers, having an OH-number of 6 or less and which is extremely stable in the presence of strong alkalis.

2. The mixed formal of polyglycol ethers of claim 1 wherein said strong acid is selected from the group consisting of sulfuric acid, phosphoric acid, p-toluene sulfonic acid, acid organic ion-exchangers and acid zeolites.

3. The mixed formal of polyglycol ethers of claim 2 wherein said strong acid is sulfuric acid.

4. The mixed formal of polyglycol ethers of claim 1 or 2 or 3 wherein said temperature is from 70° to 100° C.

5. The mixed formal of polyglycol ethers of claim 1 or 2 wherein said strong acid is a solid organic ion-exchanger or zeolite and said neutralizing step is a filtration step to remove said solid.

6. The mixed formal of polyglycol ethers of claim 1 or 2 or 3 wherein said strong acid is a liquid and said neutralizing step is conducted by the addition of a basic substance.

7. The mixed formal of polyglycol ethers of claim 6 wherein said basic substance is sodium methylate in a methanol solution.

* * * * *